United States Patent [19]

Labrum et al.

[11] 4,136,950
[45] Jan. 30, 1979

[54] MICROSCOPE SYSTEM FOR OBSERVING MOVING PARTICLES

[75] Inventors: Joseph H. Labrum, West Jordan; Donald R. Stewart, Murray, both of Utah

[73] Assignee: Labrum Engineering, Inc., West Jordan, Utah

[21] Appl. No.: 739,426

[22] Filed: Nov. 8, 1976

[51] Int. Cl.² .......................... G01P 3/36; H04N 7/18
[52] U.S. Cl. .............................. 356/28; 250/222 PC; 358/105; 358/107
[58] Field of Search .................... 356/28, 5; 358/105, 358/107; 250/222 PC

[56] References Cited

U.S. PATENT DOCUMENTS

| | | | |
|---|---|---|---|
| 3,275,744 | 9/1966 | Dietrich | 250/222 PC |
| 3,706,495 | 12/1972 | Dotson, Jr. | 356/28 |
| 3,781,468 | 12/1973 | Chomet et al. | 358/105 |
| 3,787,118 | 1/1974 | Nowicki et al. | 356/5 |
| 3,824,393 | 7/1974 | Brain | 250/222 PC |
| 3,890,462 | 6/1975 | Limb et al. | 358/107 |

OTHER PUBLICATIONS

Edmunds Scientific Co. Catalog 741; Sep. 1973; p. 153.

Primary Examiner—S. C. Buczinski
Attorney, Agent, or Firm—Mallinckrodt & Mallinckrodt

[57] ABSTRACT

A microscope system for observing moving particles makes use of a television camera for producing a continuing series of images of such particles. A source of light pulses illuminate the particles with each pulse for a period short enough to stop their movement for the camera. The light source and camera are synchronized so that the light pulses occur only between times that the camera produces image-information signals. For obtaining particle size measurements, a single light pulse during a time that the camera is not producing image-information signals is sufficient. For obtaining paticle velocity measurements, two light pulses are required so that a "double exposure" occurs at the camera during a time that the camera is not producing image-information signals.

17 Claims, 4 Drawing Figures

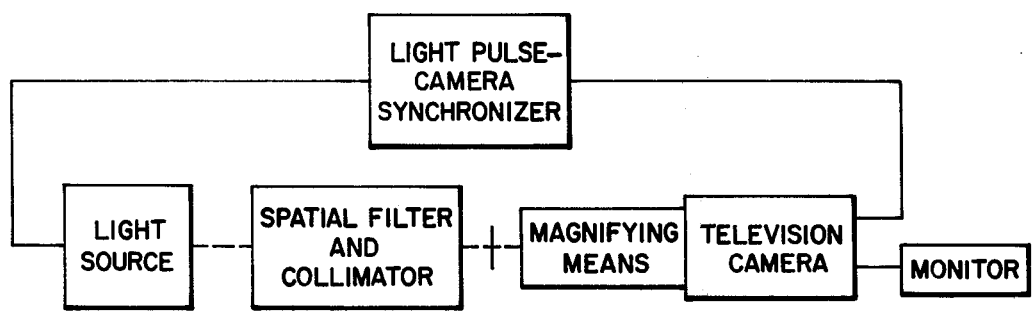
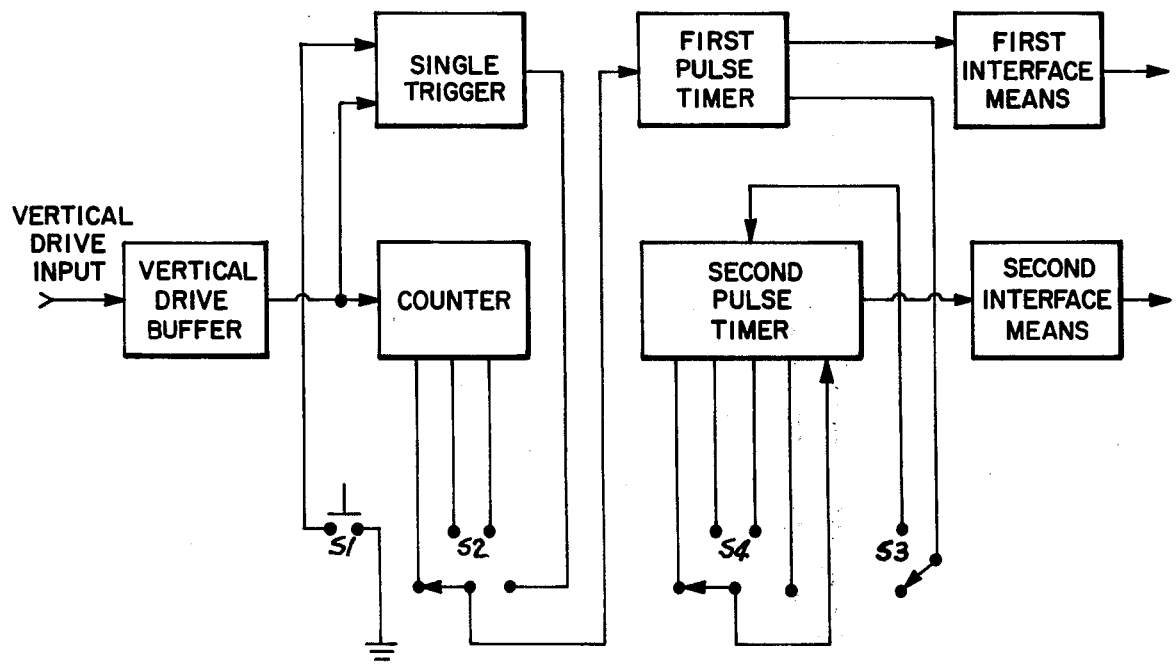
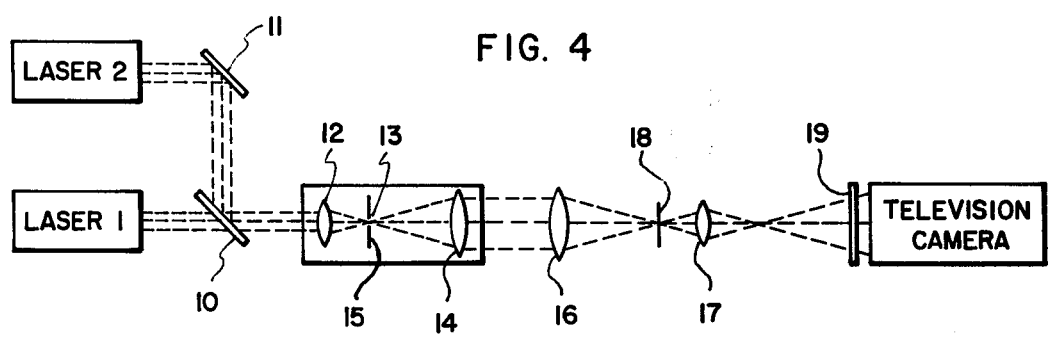

MICROSCOPE SYSTEM FOR OBSERVING MOVING PARTICLES

BACKGROUND OF THE INVENTION

1. Field

The invention is in the field of microscope systems for observing the movement of small particles.

2. State of the Art

Microscopes are well known and in wide use for viewing small particles. If the particles are rapidly moving, however, it becomes very difficult, and in most instances impossible, to study or photograph the particles. This is particularly true if it is desired to size and determine velocities of particles emanating from the nozzles of spraying devices, such as spray cans.

In designing spray cans and in developing products to be dispensed by spray cans, it is desirable to know the sizes of particles being dispensed and their velocity. This information is useful to determine whether the material is being dispensed in a manner suitable for the particular product concerned, whether the sprayed material reaches its intended target, and how much of the material is dispensed in particle sizes small enough to become suspended in the air and inhaled.

A system has been developed recently which utilizes a television camera and a laser to observe particles in aerosol sprays for obtaining the desired information. The laser produces a series of short, high energy pulses, which travel through an image plane to the television camera. The laser acts as a strobe to stop the action of the particles as they move, and produces a free running series of pulses. However, many of the pictures produced by the television camera are useless. This is because a light source such as a laser produces a large amount of electromagnetic energy which is radiated along with the light from the light source. This electromagnetic radiation effects the electronics in the television camera so as to destroy a portion of the picture when the pulse occurs. Also, each time a light pulse occurs a new picture is taken so that many pictures produced by the camera are half one picture and half another. Distortion of the particles in the pictures is often great, resulting in poor particle resolution. Moreover, the system is useful only for sizing the particles. No system has been available for measuring the velocities of the particles.

SUMMARY OF THE INVENTION

According to the invention, a system for observing moving particles comprises a television camera which includes an image-sensitive device, having short term storage capability, and a scan system for producing electrical image-information signals representative of the image sensed by the device. The scan system is adapted to successively scan the device, with blank periods interposed between successive scans, no image-information signals being produced during the blank periods. The storage capability of the image-sensitive device is such that an image is stored until the device is scanned and the image is converted to electrical image-information signals. This merely defines the normal television camera in use today. The camera is provided with means for synchronizing it with a light source which produces a series of light pulses, each pulse having a duration less than the duration of the blank period of the television camera. The synchronization is such that the light pulses occur during a blank period of the television camera, but not during the time image-information signals are being produced by the scan system of the camera. In this way, each picture of the camera is clear and has good contrast between particle images and the background. The camera electronics have time to settle down before the scan system of the camera begins producing image-information signals, and new pictures are not taken in the middle of an image scan. Synchronization may be controlled so that the light pulses occur during selected blank periods of the camera, i.e. during every second, every fourth, or during some other selected sequence of blank periods. In this way, an image created on the image-sensitive device by a light pulse occuring during one blank period is allowed to substantially fade before the next image is created. This permits clearer pictures to be obtained because traces of images from a previous blank period do not appear along with the new images formed. An object plane is located between the light source and the camera and magnifying means is provided to focus the camera on the object plane. Means are provided to monitor the picture of the television camera, either visually or otherwise, to obtain desired information, e.g. as to particle size distribution. For measuring particle size distribution, the synchronizing means is adapted to produce only a single pulse during blank periods in which light pulses occur.

In order to measure velocity of the particles, the synchronizing means is adapted to cause the light source to produce two light pulses separated by a preset time interval during those blank periods in which light pulses occur. The two pulses create a double exposure effect on the image-sensitive device of the camera. Knowing the time between the two pulses and measuring the distances that particles have moved in the picture between the two exposures, the velocities may be calculated. The two pulses may conveniently be provided by two light pulse sources arranged so that the light from each source travels the same path through the object plane into the camera. Lasers are a convenient source of light pulses.

To improve the resolution of the particles in the pictures when using coherent light sources such as lasers, it is preferred that the light from the light source be passed through a collimator and spatial filter before arriving at the object plane. The spatial filter preferably eliminates all but zero order diffraction patterns from the light.

A shading corrector may be added ahead of the camera's image-sensitive device to compensate for differences in background light intensity over the cross-section of the light reaching the device. This provides more even picture illumination.

THE DRAWINGS

The best mode presently contemplated for carrying out the invention is illustrated in the accompanying drawings, in which:

FIG. 1 is a block diagram of the basic system of the invention;

FIG. 2, a block diagram of the light pulse-camera synchronizer of FIG. 1;

FIG. 3, a circuit diagram of the light pulse-camera synchronizer; and

FIG. 4, a diagramatic representation of the optical portion of the system showing arrangement of the lenses for the spatial filter and collimator and magnifying means of FIG. 1.

DETAILED DESCRIPTION OF THE ILLUSTRATED EMBODIMENTS

Figure 3:
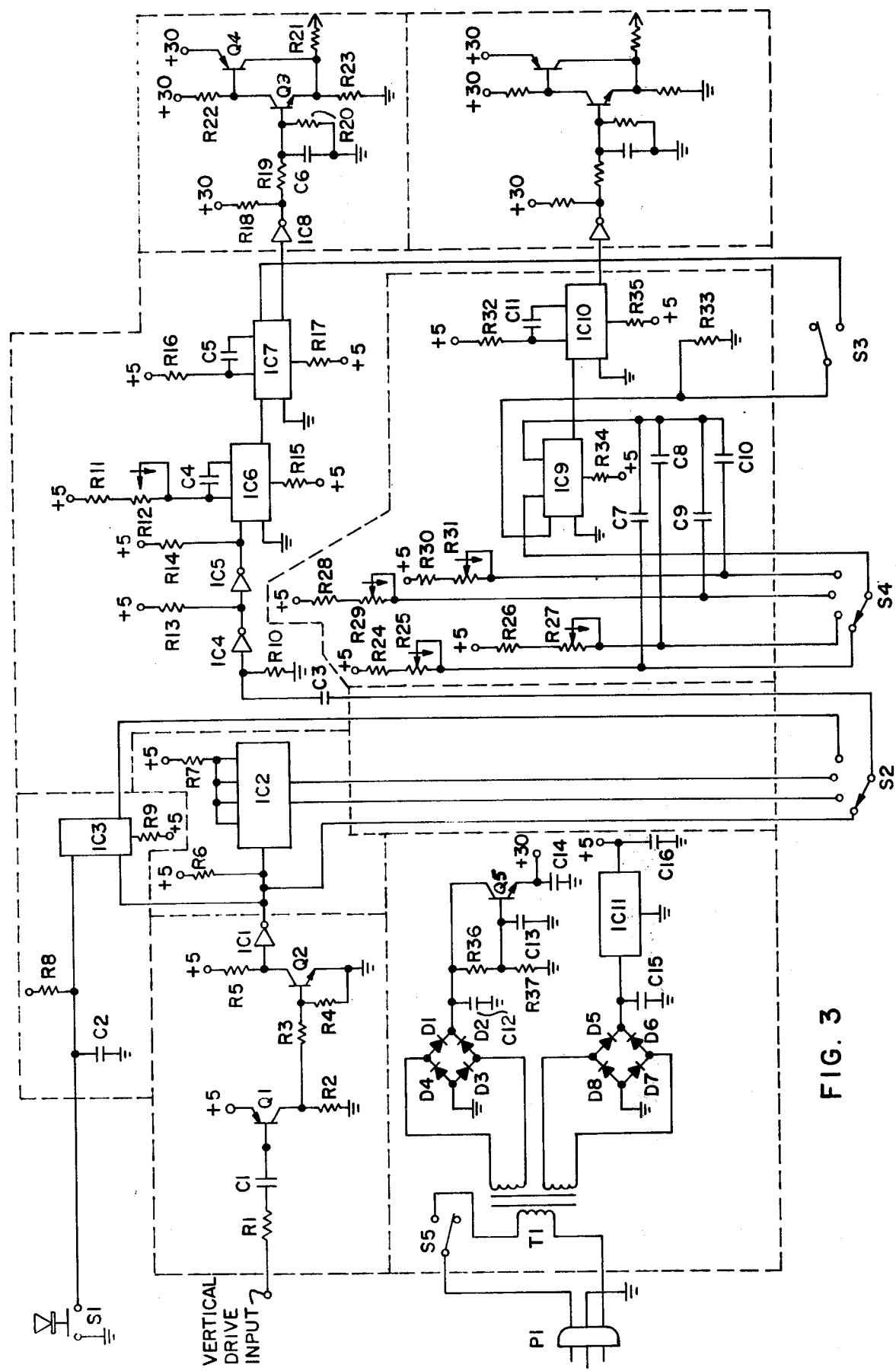

As illustrated, a preferred microscope system for observing moving particles utilizes an ordinary television camera. The usual television camera has an image-sensitive device and a scan system for producing electrical image-information signals representative of the image sensed by the device. The scan system successively scans the device and between scans there is a blank period during which there are no image-information signals produced. One complete image scan of the device generally includes a number of scans from left to right across the image-sensitive device. The scans start at the top and work their way to the bottom of the device. The blank period represents the time necessary for the scan system to ready itself to begin a completely new scan at the top of the image-sensitive device after it has completed scanning to the bottom of the device, and usually includes several scans at the top of the device where no image informagion signals are produced. The blank period of the camera is initiated in the scanning system by an electrical pulse, generally called a vertical drive pulse.

The image-sensitive device also has a storage capability whereby the image sensed by the device is stored until the device is scanned and the image is converted to electrical image-information signals.

In order to observe moving particles it is necessary to illuminate the particles by a pulse of light short enough to stop the action of the particles on the image-sensitive device. To stop the motion of the usual particles as dispensed from the nozzle of an aerosol can, a light pulse duration of less than 200 nanoseconds and preferably less than 30 nanoseconds should be used. The presently preferred light source is a nitrogen laser which can produce a short, high energy light pulse. A satisfactory nitrogen laser is made by Laser Energy, Inc. and designated as $N_2$-50. Lasers of this type have a light pulse length of approximately 10 nanoseconds. This is sufficient to observe a 1 micron particle traveling at a speed of 10 meters per second. A particle may be observed clearly if the particle moves less than one-tenth its diameter during the exposure time. Such movement does not cause appreciable blurring of the particle. This length of light pulse has been found satisfactory for observing particles dispensed from aerosol cans.

Along with the light, a laser produces a large amount of electromagnetic energy which disturbs the signal from the television camera and causes distortion in any image-information signals. It has been discovered that by synchronizing the light source and the television camera so that the light pulses occur only during the blank period of the camera, the distortion has settled out of the camera by the time the image-information signals are produced by the scan system. For best results, there should be at least a 100 microsecond interval between a light pulse and the start of the production of image-information signals.

For measuring velocity of the moving particles, two pictures are superimposed (double exposed) on the image-sensitive device of the television camera. The pictures are taken a known time interval apart so that by measuring the distance a particle has moved, its velocity may be determined. The two exposures appear on the same picture from the television camera and are made by two light pulses, each light pulse causing an exposure.

In order for both exposures to appear on the same picture, both light pulses must occur during the same blank period of the camera. Further, these two exposures, or light pulses, must be close enough together so that the moving particles have not moved out of the picture area between the two exposures and so that the particles remain identifiable from one exposure to the next. Thus, the time interval between exposures depends upon the velocity of the particles being observed. For measuring velocity of particles dispensed from aerosol spray cans, time intervals as small as 0.5 microseconds may be desirable.

The presently available light pulse sources, such as the laser referred to above, cannot produce light pulses as close together as is necessary to make the two exposures. Therefore, two light pulse sources are included in the light source as indicated by the two lasers shown in FIG. 4. One laser produces the first light pulse and the second laser produces the second light pulse the predetermined time after the first pulse. The timing function is performed by the synchronizing means.

The image-sensitive device of the television camera has a storage capability so that an image is stored until the device is scanned and the image is converted to the electrical image-information signals. Thus, the image produced on the image-sensitive device by a light pulse or by the double light pulses as discussed above, remains until the device is scanned and the image-information signals produced. The scan performs an erasing function on the device.

With the television cameras in use today, an image is generally not completely erased after only one scan of the image-sensitive device. A faint image remains for several scans. In normal light situations, these faint images cannot be detected by the eye in a television picture. This is because the bright new images constantly being produced on the device are so much brighter in the resulting television picture than the remains of the past images. In a system such as the present one, however, even though the light source produces a high energy light pulse (the lasers mentioned may produce up to 50 kilowatts of peak power per pulse) the light that actually reaches the television camera is relatively small. With the resulting low level of illumination reaching the camera, the brightness of the original images produced are not of such magnitude that past images remaining after a scan or two are drowned out. Thus, the images that remain after a scan are noticeable in the resulting television picture and result in a cluttered and sometimes unclear picture from which it is difficult to obtain measurements.

To eliminate this problem, it is desirable to have the light source produce the light pulses only during selected blank periods, such as every second, every fourth or every eighth blank period. With the illustrated system, improvement in pictures are obtained by using up to every eighth blank period, but the picture is not improved much by using larger periods. Since most television cameras scan the image-sensitive device sixty times each second, a flicker in the picture starts to become noticeable when allowing the image to fade for eight scans and becomes more pronounced above that.

The light-pulse camera synchronizer performs the job of synchronizing the light pulses to the camera blank periods and of timing and controlling the interval between the pulses when two light pulses are used.

The circuitry of the light-pulse camera synchronizer is shown by block diagram in FIG. 2.

As mentioned previously, the television camera produces a vertical drive pulse at the start of each blank period. In most television cameras, this pulse is separated from the image information and other signals produced by the camera and there is a point within the camera electronics where this signal may be obtained. The point for obtaining this signal will vary from camera to camera, but a person skilled in television camera art would be able to locate such a point. A few cameras even provide a terminal for the output of this signal. In a few cameras, additional circuitry may be needed to isolate the vertical drive pulse from the image information and other signals produced by the camera. In any event, this vertical drive pulse from the television camera is connected to the vertical drive buffer which provides a high impedance so as not to load the television camera electronics. The buffer provides a coincident, similar pulse to the rest of the synchronizer circuitry. The pulses from the vertical drive buffer enter the counter which counts the number of pulses which occur. The counter provides several outputs: an output each time a pulse is received from the vertical drive buffer, an output each four pulses received, and an output each 8 pulses received. Of course, other progressions could be used, but the one mentioned is most convenient for use with a binary counter.

The pulses from the vertical drive buffer also go to the single trigger which produces a pulse coincident with the pulse from the vertical drive buffer, but only upon manual command caused by the manual closing of the single trigger switch S1.

Rotary selector switch S2 selects either one output from the counter or the output from the single trigger and connects it to the first pulse timer. The first pulse timer produces a pulse with pulse width adjusted to be compatible with the light source trigger circuitry and occuring at the desired time during the blank period when the light source is to produce a light pulse. The output of the first timer is connected to the first interface means which provides the pulse with the correct amplitude and driving impedance for the light source trigger circuitry. This is all that is necessary for a single light pulse system which can be used to determine particle size distribution.

For the two light pulse system, an output from the first pulse timer is connected to selector switch S3. This switch selects either a single light pulse mode for size distribution determination, in which case this output from the first pulse timer is not connected to anything, or the double light pulse mode for measuring particle velocities, in which case the switch S3 connects this output of the first pulse timer to the input of the second pulse timer.

The second pulse timer produces an output similar to the output of the first pulse timer, but delayed therefrom.

There are four intermediate outputs from the second timer connected to selector switch S4. One output provides a delay time of 0.5 microseconds, one a delay time of 5 microseconds, one a delay time of 100 microseconds, and one allows for adjustment of the delay time from 100 microseconds to about 1000 microseconds. The desired time delay is selected by switch S4 and the timer then gives an output similar to that given by the first pulse timer, but delayed the desired time. The output of the second timer is connected to the second interface means which, like the first interface means, gives the pulse the correct amplitude and driving impedance to trigger the light source for the second light pulse.

The presently preferred circuitry of the synchronizer is shown in detail in FIG. 3. It should be realized that various circuit arrangements could be used to produce the same results.

The vertical drive pulse taken from the television camera enters the circuitry as labeled. It enters through resistor R1 and capacitor C1 which couple the pulse to the base of transistor Q1 which, in conjunction with resistor R2, operates as a common emitter amplifier. The resistance R1 is chosen to present a high impedance to the vertical drive pulse so as not to load the camera. This resistance will usually be in the range of at least 10k ohms.

A pulse coincident with the entering vertical drive pulse, but inverted, appears across resistor R2 and is connected through resistor R3 to transistor Q2 which, in conjunction with resistors R4 and R5, operates as a common emitter amplifier with the pulse, inverted again, appearing across Q2 and being fed to an integrated circuit inverter IC1. The vertical drive pulse from the camera is generally a negative going pulse. The pulse from IC1 is therefore a positive going pulse and is the output of the vertical drive buffer circuitry.

The output from IC1 is fed to the input of an integrated circuit binary counter IC2. Resistors R6 and R7 are provided to properly bias the counter. IC2 counts the number of pulses it receives and produces an output pulse for every two pulses, every four pulses, every 8 pulses and every 16 pulses. In the circuit as shown, only the output pulses representing every fourth and every eighth pulse is used. These two outputs of IC2 are connected to selector switch S2. Also connected to switch S2 is the input of IC2 which is the output IC1 and represents an output pulse for every vertical drive pulse. Switch S2 is also connected to the single trigger circuitry made up of IC3, resistor R8 and capacitor C2.

Switch S2 selects one of the four connections just mentioned and connects it to the first pulse timer. Thus, the pulse timer can be connected to receive every pulse entering IC2, a pulse every four pulses counted by IC2, a pulse every eight pulses counted by IC2, or a pulse generated by the single trigger circuit.

The output pulses from IC1, as well as being directed to IC2 and S2, are also connected to IC3 of the single trigger circuitry. Switch S1 initiates the single trigger by setting IC3 so that upon the next pulse it receives from the vertical drive buffer, it will produce a similar coincident pulse. Resistors R8 and R9 properly bias IC3 and capacitor C2 eliminates any contact noise generated by S1. Only one pulse is produced by IC3 each time switch S1 is depressed.

The signal selected by selector switch S2 enters the first pulse timer. Capacitor C3 and resistor R10 from a differentiator which produces a narrow positive going pulse on the positive leading edge of the pulse entering through switch S2. Inverter IC4 acts as a buffer to prevent loading of the differentiator and invertor IC5 inverts the inverted pulse so that it is again a positive pulse. The positive pulse output of IC5 enters IC6, an integrated circuit monostable multivibrator. When the input to IC6 goes positive, the output goes low and remains low for a period of time determined by the values of R11, R12, and C4. At the end of the time period set by R11, R12, and C4, the output of IC6 goes positive. Thus, IC6 produces a positive pulse a predetermined time after the pulse enters IC6. The resistance of R12 is adjustable so that the time delay may be adjusted. R13, R14, and R15, insure proper bias for the integrated circuits. If the first light pulse is to occur coincident with the vertical drive pulse (start of blank period) as will normally be the case, IC6 will be set for a zero time delay.

The positive going output of IC6 enters IC7 and causes one output of IC7 to go high and one to go low. The time constant of IC7 is determined by resistor R16 and capacitor C5. This time constant is adjusted so that the positive and negative going pulses from IC7 are of a duration compatible with the trigger circuitry of the light source. For the lasers mentioned previously, the pulse width should be about 350 nanoseconds. Resistor R17 insures proper bias of IC7. The positive and negative pulse outputs from IC7 are the outputs of the first pulse timer, and are pulses adjusted in pulse width to be compatible with the laser trigger circuitry (internal part of the laser) and delayed from the beginning of the blank period of the camera so as to be positioned at the desired time during the blank period.

The negative going pulse output from the first pulse timer (output of IC7) is connected to the first interface means. The negative pulse is inverted by integrated circuit inverter IC8. The output of IC8 is of an open collector type which allows the output voltage to be higher than the normal supply voltage of the integrated circuit. R18 is a load resistor with a +30 volt supply. The output pulse from IC8 is thus a positive pulse of approximately 30 volts. This pulse is coupled through resistor R19 to the base of transistor Q3. Resistors R19 and capacitor C6 are arranged to prevent any circuit oscillations. Resistor R20 is a bias resistor.

Transistors Q3 and Q4 are connected to form a bootstrapped emitter follower output stage. With this arrangement, the impedance of the emitter of Q3 is near 0 ohms so that the output impedance of the circuit equals the resistance of R21 which, for the lasers specified, should be approximately 75 ohms. With the arrangement of resistors R22 and R23, the output of the first interface means is a positive pulse of about 30 volts with a width of 350 nanoseconds. The output impedance is about 75 ohms. This is the pulse that is needed to trigger the laser. The output of the interface means is connected directly to the laser.

The positive going pulse output of the first pulse timer is connected to switch S3. If single light pulse operation is desired, the switch is open so that the positive pulse is not connected to the second pulse timer. For dual light pulse operation, S3 is closed, connecting the positive output pulse of the first pulse timer to the input of the second pulse timer. The pulse enters the input of IC9, a monostable multivibrator similar to IC6. This causes the output of IC9 to go low. Rather than the single time delay network of IC6 of the first pulse timer, IC9 has four different time delay networks. The desired network is selected by selector switch S4. Each network is similar in arrangement but component values differ so that different delay periods are achieved. The first delay network comprises resistors R24 and R25 and capacitor C7, the second, resistors R26 and R27 and capacitor C8, the third, resistors R28 and R29 and capacitor C9, and the fourth, resistors R30 and R31 and capacitor C10. The actual delay times of each network will vary depending upon the use of the system, but in the presently preferred embodiment for measuring velocity of particles expelled from aerosol cans, the first network provides a delay of 0.5 microseconds, the second, a delay of 5 microseconds, the third a delay of 100 microseconds, and the fourth is adjustable by adjusting R31, to between 100 and 1000 microseconds. After the selected delay time, the output of IC9 which went low at the beginning of the positive input pulse, goes positive initiating the similar integrated circuit monostable multivibrator of IC10. The time constant of IC10 is adjusted by resistor R32 and capacitor C11 to provide a negative output pulse of 350 nanoseconds width, upon receipt of the positive going pulse from IC9. Resistors R33, R34, and R35 provide a proper bias for the integrated circuits. The negative pulse output of IC10 is the output of the second pulse timer. This is connected to the second interface means which is identical to the first interface means and operates as explained for that means. The output is a 350 nanosecond wide, 30 volt positive pulse which triggers the second laser. The pulse occurs the selected delay time after the pulse from the first interface means.

The circuit shown also contains a power supply comprising a transformer T1 with primary adapted to be connected to a 120 volt A.C. line by means of plug P1 and on-off switch S5. Transformer R1 has two secondaries. One secondary is connected to full wave rectifying bridge comprising diodes D1, D2, D3, and D4. Capacitor C12 is a filtering capacitor. Resistor R36 and R37 form a voltage divider for adjusting the voltage supplied to the base of transistor Q5. Capacitor C13 protects Q5 from any transient voltage spikes that may occur. Q5 is arranged with capacitor C14 as an emitter follower. The output across C14 will be equal to the voltage on the base of Q5. The output voltage is adjusted to be approximately 30 volts and serves as the power supply for the two interface means at terminals marked +30.

The other secondary of transformer T1 is connected to full wave rectifying bridge comprising diodes D5, D6, D7, and D8. Capacitor C15 is a filtering capacitor. IC11 is an integrated circuit voltage regulator. The input to IC11 is the voltage across capacitor C15. The output of IC11 is a regulated 5 volts and appears across capacitor C16. This serves as the power supply for all portions of the circuit marked +5.

Some of the integrated circuits may be conveniently contained in a single package. For example, the inverters labeled IC1, IC4, IC5, IC8, and the inverter corresponding to IC8 in the second interface means, may all be contained in a single package, which may be a Texas Instruments S.N. 7416. The monostable multivibrators of the pulse timing means may also be in a single package. IC6 and IC7 may conveniently be a single Texas Instruments S.N. 75221, as may IC9 and IC10. Satisfactory integrated circuits for IC2, IC3 and IC11 may be a Texas Instruments S.N. 74163, a Texas Instruments S.N. 7474 and a Motorola MC 7805C, respectively.

The light source and camera are arranged so that the light from the light source is directed through an object plane, through magnifying means, to the camera. The camera is focused through the magnifying means so that anything in the object plane will be magnified and focused on the camera image-sensitive device. A spatial filter and collimator is preferably placed between the laser and the object plane to collimate and remove all but zero order diffraction patterns from the light. Although any type of lens arrangement could be used, that illustrated diagramatically in FIG. 4 is preferred.

In front of laser 1 is a mirror designed to reflect 50% of the light from the laser striking it and to transmit 50% of the light striking it. Thus, 50% of the light striking mirror 10 passes through it to the rest of the optical system. A 100% reflective mirror 11 is located in front of laser 2. The light from laser 2 is reflected by mirror 11 toward mirror 10. Of the light reflected from mirror 11 striking mirror 10, 50% is reflected into the optical system and 50% is transmitted. The mirrors are adjusted so that the transmitted light from laser 1 and the reflected light from laser 2 will travel exactly the same path through the optical system. The two lasers and associated mirrors make up the light source.

The light from the lasers will first enter the focusing lens 12 of the collimator and spatial filter. Lens 12 focuses the light by causing the light to converge at a point 13, before diverging as shown, to collimator lens 14. Actually, lens 12 produces a diffraction pattern of concentric rings of light, rather than the single spot of light 13. This is caused by various degrees of light diffraction that occur. The center spot 13 comprises light of substantially equal phase and is known as zero order diffraction. This spot contains about 75% to 80% of the light energy of the light beam. Light of different phases will be concentrated in different rings of the diffraction patterns surrounding center spot 13. By placing a plate 15 with an aperture of approximately 10 microns so that the aperture is positioned coincident with spot 13, light of substantially single phase represented by spot 13 is allowed to pass, but all other light represented by the rings about the center is blocked and does not continue through the optical system. Single phase light in the system substantially eliminates the interference patterns that would otherwise occur around the small particles being observed and thus greatly improves the resolution of the system.

The light passed by the plate 15, which comprises the spatial filter, is collimated by lens 14. Thus, the light is caused to travel in parallel rays. In the present system, the focusing lens 12 is approximately 5 millimeters in diameter and the collimating lens is approximately 50 millimeters in diameter.

The collimator and spatial filter is needed with coherent light sources such as lasers because with the narrow range of light wavelengths produced by such sources, the interference and diffraction patterns that are produced are very pronounced and can substantially effect the resolution of the system.

A condensing lens 16 focuses the light through the object plane to objective lens 17 which in turn focuses any object present in the image plane on the image-sensitive device of the television camera as a magnified image. The objective lens is positioned so that the object plane 18 focused on the camera screen is ahead of the converging point 19 of the light from condensing lens 16 making a larger field of illumination at the object plane.

The inclusion of the condensing lens 16 while not necessary for an operable system, greatly increases the contrast and focus of the pictures produced by the system. If the light from the object plane is directed to the objective lens in a cone formation, many more of the higher order diffraction patterns caused by the observed particles will be collected by the lens than if the light entered the objective in parallel formation. These higher order diffraction patterns are required to provide good contrast between the observed particles and the background and to provide sharp outlines of the observed particles.

The objective lens 17 is selected to give the desired magnification. Two objective lenses could be used in series to provide even greater magnification than can be obtained with a single objective.

Another factor affecting the resolution of the system is the wavelength of the light being used for illumination. With a given lens system, the shorter the wavelength, the greater the resolution of small particles. The nitrogen lasers described, produce a short wavelength light of about 337.1 nanometer. If a light source producing longer wavelength light is used, resolution is decreased.

The illustrated system was designed for use with particles ranging in size from about one-half micron to around several hundred microns, (particles dispensed from aerosal cans are usually in the range from about one-half micron to about 50 microns) but could easily be used with larger particles. The size of the particles to be observed will determine the amount of magnification needed, if magnification is needed at all, and the size of the illuminated object plane required.

If desired, a shading corrector 19 may be positioned immediately in front of the image-sensitive camera device of the camera. This corrects for differences in background brightness so that the background looks uniformly bright to the camera. The filter may be conveniently made from a fine grain flass plate film which is placed in position and exposed by the normal background light (light without any object being observed in the object plane and then developed as a negative. Some trial and error is necessary to get the proper exposure and development time but once proper contrast is achieved on the plate, very effective shading correction is obtained.

With the optical system as illustrated and described, very little outside light reaches the camera image-sensitive device. Essentially all light reaching the device is that generated by the lasers.

The pictures taken by the television camera are monitored to obtain the useful information desired. The monitor may be the usual television monitor which displays the picture on a television picture tube for visual inspection. It is preferred that the camera picture also be recorded on video tape so that it may be played back through the television monitor a frame at a time for detailed visual analysis. Such analysis would include the visual sizing of the particles and counting the number of particles within certain size ranges. Measuring the distance traveled by each particle between the two light pulses and dividing by the time delay between the two pulses, gives the velocity of each particle.

While the velocity measurements currently must be made by visual inspection and calculations, Bausch and Lomb currently produce a computer which they market under the name Omnicon which can take the information from the television camera and calculate particle size and size distribution. The computer in some cases could thus be the monitoring means.

From the above, it can be seen that the invention is also concerned with a method of measuring the velocity of moving particles by a series of steps as indicated herein and in the method claims that follow.

Whereas the invention has been described with reference to a specifically illustrated preferred embodiment, it should be realized that various changes may be made without departing from the disclosed inventive subject matter particularly pointed out and claimed herebelow.

We claim:

1. A microscope system for observing and determining the velocity of moving particles, comprising a television camera which includes an image sensitive device, having short term storage capability, and a scan system for producing electrical, image-information signals representative of the image sensed by said device, the scan system being adapted to successively scan said device, with blank periods interposed between successive scans, no such signals being produced during the blank periods, and the storage capability of said image-sensitive device being such that an image is stored until said device is scanned and the image is converted to electrical, image-information signals; a light source adapted to produce a series of light pulse pairs, the second pulse of each pair occurring a present time interval after the first pulse of that pair, and each pulse pair having a duration less than the duration of a blank period of the camera; means for synchronizing the light source and the camera, so that any light pulse pairs occur during a blank period of the camera; magnifying means for focusing the camera on an object plane between the light source and the camera, so that the camera sees a magnified image of anything placed in the object plane; and means for monitoring the camera picture to obtain desired information.

2. A microscope system according to claim 1, wherein the synchronizing means is adapted to cause light pulse pairs to occur during blank periods of the camera which immediately follow a predetermined number of blank periods without light pulse pairs.

3. A microscope system according to claim 2, wherein the synchronizing means is adapted to cause light pulse pairs during every fourth blank period.

4. A microscope system according to claim 1, wherein shading corrector means is located between the camera and the magnifying means, so that the camera sees a field of substantially uniform brightness.

5. A microscope system according to claim 4, wherein the shading corrector is a piece of film that has been exposed in position between the camera lens and magnifying means and has been developed as a negative.

6. A microscope system according to claim 5, wherein the film is a glass photographic plate.

7. A microscope system according to claim 5, wherein the lasers are nitrogen lasers.

8. A microscope system according to claim 1, wherein a collimator and spatial filter is positioned between the light source and the object plane, so that the light reaching the object plane is collimated light with substantially all but zero order diffraction patterns removed therefrom.

9. A microscope system according to claim 8, wherein the spatial filter and collimator includes a focusing lens, a plate having an aperture and arranged so that the aperture passes the light contained in the center spot of a diffraction pattern but so that the plate blocks the remainder of the diffraction pattern when such pattern is focused on the plate by the focusing lens, and a collimating lens which collimates the light passed by the aperture.

10. A microscope system according to claim 1, wherein the light source is a laser.

11. A microscope system according to Claim 10, wherein the laser is a nitrogen laser.

12. A microscope system according to claim 7, wherein each of the two light pulse sources is a laser.

13. A microscope system for observing and determining the velocity of moving particles, comprising a television camera which includes an image sensitive device, having short term storage capability, and a scan system for producing electrical, image-information signals representatives of the image sensed by said device, the scan system being adapted to successively scan said device, with blank periods interposed between successive scans, no such signals being produced during the blank periods, and the storage capability of said image-sensitive device being such that an image is stored until said device is scanned and the image is converted to electrical, image-information signals; two laser light sources each adapted to produce a series of light pulses, one of said laser light sources being connected to produce a light pulse a preset time interval after the other laser light source produces a light pulse, the total duration of both pulses and the time interval between the pulses being less than the duration of a blank period of the camera; means for synchronizing the laser light sources and the camera, so that any light pulses occur during a blank period of the camera; magnifying means for focusing the camera on an object plane between the light source and the camera, so that the camera sees a magnified image of anything placed in the object plane; a collimator and spatial filter positioned between the light source and the object plane so that the light reaching the object plane is collimated light with substantially all but zero order diffraction patterns removed therefrom; and means for monitoring the camera picture to obtain desired information.

14. A microscope system according to claim 1, wherein the light source includes two light pulse sources arranged so that one source produces the first light pulse of the light pulse pair and a second source produces the second light pulse of the light pulse pair, and means are included for aligning the light from the two pulse sources so that it travels the same path through the object plane and into the camera.

15. A microscope system according to claim 7, wherein the aligning means causes the light from the two pulse sources to travel the same path through collimator and spatial filter.

16. A method of measuring the velocity of moving particles, comprising the steps of directing the particles through an object plane of a television camera, whereby they are focused on the image-sensitive device of the television camera; illuminating the particles in said object plane by a pulse of light short enough to stop the action of the particles, thereby creating an image of the particles on the image-sensitive device; illuminating the particles by a second pulse of light short enough to stop the action of the particles at a time after the first light pulse, so that some of the particles in the object plane at the time of the first pulse are still in the object plane at the time of the second pulse, said second pulse creating a second image of the particles on the image-sensitive device; causing a scan system to scan the image-sensitive device only after both light pulses have occurred and to convert the images on the image-sensitive device to electrical image-information signals; converting the electrical signals into information from which the distances traveled by a particle between the two images of said particle can be determined; determining the distance such a particle has traveled between the two images, and dividing the distance obtained by the time between the two light pulses to determine the velocity of the particle.

17. A method according to claim 16, including the step of storing the electrical image-information signals produced by the scan system; and repeating the several enumerated steps prior to converting the electrical signals into information from which the distance traveled is determined, more than once each second during the time particles are in the object plane.

* * * * *

UNITED STATES PATENT OFFICE
CERTIFICATE OF CORRECTION

PATENT NO. : 4,136,950
DATED : January 30, 1979
INVENTOR(S) : Joseph H. Labrum, et al It is certified that error appears in the above-identified patent and that said Letters Patent are hereby corrected as shown below:

Claim 1, Column 11, line 15, "present" should read --preset--.

Claim 7, first line of claim, "5" should read --13--.

Claim 12, first line of claim, "7" should read --14--.

Claim 13, column 12, line 1, "resentatives" should read --resentative--.

Claim 15, first line of claim, "7" should read --13--.

Signed and Sealed this

Twenty-second Day of May 1979

[SEAL]

Attest:

RUTH C. MASON
Attesting Officer

DONALD W. BANNER
Commissioner of Patents and Trademarks